US012668747B2

(12) United States Patent
Beato

(10) Patent No.: US 12,668,747 B2
(45) Date of Patent: Jun. 30, 2026

(54) METHANOL TO OLEFIN (MTO) PROCESS

(71) Applicant: HALDOR TOPSØE A/S, Kgs. Lyngby (DK)

(72) Inventor: Pablo Beato, Nordhavn (DK)

(73) Assignee: TOPSOE A/S, Kgs. Lyngby (DK)

( * ) Notice: Subject to any disclaimer, the term of this patent is extended or adjusted under 35 U.S.C. 154(b) by 245 days.

(21) Appl. No.: 18/027,017

(22) PCT Filed: Sep. 24, 2021

(86) PCT No.: PCT/EP2021/076369
§ 371 (c)(1),
(2) Date: Mar. 17, 2023

(87) PCT Pub. No.: WO2022/063992
PCT Pub. Date: Mar. 31, 2022

(65) Prior Publication Data
US 2023/0365871 A1     Nov. 16, 2023

(30) Foreign Application Priority Data

Sep. 25, 2020   (DK) ............................ PA 2020 01109
Sep. 25, 2020   (DK) ............................ PA 2020 01110
Sep. 25, 2020   (EP) ..................................... 20198386

(51) Int. Cl.
*C07C 1/20*          (2006.01)
*C07C 1/00*          (2006.01)
(Continued)

(52) U.S. Cl.
CPC ................. *C10G 3/49* (2013.01); *C07C 1/00* (2013.01); *C07C 1/20* (2013.01); *C07C 1/24* (2013.01);
(Continued)

(58) Field of Classification Search
CPC ........ C10G 3/49; C10G 69/12; C10G 69/126; C10G 2300/1092; C10G 2400/08;
(Continued)

(56) References Cited

U.S. PATENT DOCUMENTS 4,021,502 A     5/1977   Plank et al.
4,211,640 A     7/1980   Garwood et al.
(Continued)

FOREIGN PATENT DOCUMENTS

CN          104059682 A     9/2014
CN          107963953 A     4/2018
(Continued)

OTHER PUBLICATIONS

U.S. Appl. No. 18/727,130, filed Jul. 8, 2024, Niels Christian Schjødt.
(Continued)

*Primary Examiner* — In Suk C Bullock
*Assistant Examiner* — Jason Y Chong
(74) *Attorney, Agent, or Firm* — Boone IP Law

(57) ABSTRACT

A process for producing an olefin stream, said process comprising passing a feedstock stream comprising oxygenates over catalyst comprises a zeolite with a framework having a 10-ring pore structure, in which said 10-ring pore structure comprises a unidimensional (1-D) pore structure, such as *MRE, at a pressure of 1-25 bar and a temperature of 240-360° C. The olefin stream may be converted to jet fuel, particularly sustainable aviation fuel (SAF) by further oligomerization and hydrogenation.

24 Claims, 6 Drawing Sheets

(51) Int. Cl.

| | |
|---|---|
| *C07C 1/24* | (2006.01) |
| *C10G 3/00* | (2006.01) |
| *C10G 69/12* | (2006.01) |
| *C07C 11/02* | (2006.01) |
| *C07C 11/04* | (2006.01) |
| *C07C 11/06* | (2006.01) |

(52) U.S. Cl.
CPC ............ *C10G 69/126* (2013.01); *C07C 11/02* (2013.01); *C07C 11/04* (2013.01); *C07C 11/06* (2013.01); *C10G 2300/1092* (2013.01); *C10G 2400/08* (2013.01)

(58) Field of Classification Search
CPC .. C10G 50/00; C07C 1/00; C07C 1/20; C07C 1/24; C07C 11/02; C07C 11/04; C07C 11/06; Y02P 30/20
See application file for complete search history.

(56) References Cited

U.S. PATENT DOCUMENTS

| | | | |
|---|---|---|---|
| 4,227,992 | A | 10/1980 | Garwood et al. |
| 4,433,185 | A | 2/1984 | Tabak |
| 4,456,779 | A | 6/1984 | Owen et al. |
| 4,476,338 | A | 10/1984 | Chang et al. |
| 4,482,772 | A | 11/1984 | Tabak |
| 4,613,719 | A | 9/1986 | Kukes et al. |
| 4,684,757 | A | 8/1987 | Avidan et al. |
| 4,740,645 | A | 4/1988 | Garwood et al. |
| 4,851,606 | A | 7/1989 | Ragonese |
| 4,898,717 | A | 2/1990 | Hsia et al. |
| 5,146,032 | A | 9/1992 | Harandi |
| 5,177,279 | A * | 1/1993 | Harandi ................... C10G 3/49 585/329 |
| 5,254,767 | A | 10/1993 | Dwyer |
| 5,268,515 | A | 12/1993 | Irvine |
| 6,372,949 | B1 | 4/2002 | Brown et al. |
| 6,403,854 | B1 | 6/2002 | Miller |
| 7,482,300 | B2 | 1/2009 | Lai et al. |
| 8,198,338 | B2 | 6/2012 | Shulenberger |
| 8,524,970 | B2 | 9/2013 | Rothaemel et al. |
| 9,505,670 | B2 | 11/2016 | Vijayakumari |
| 9,957,449 | B2 | 5/2018 | Luebke et al. |
| 11,060,036 | B2 | 7/2021 | Sorensen |
| 11,492,310 | B2 | 11/2022 | Olayiwola |
| 2002/0103406 | A1 | 8/2002 | Mathys et al. |
| 2006/0161035 | A1 | 7/2006 | Kalnes |
| 2007/0131581 | A1 | 6/2007 | Lai et al. |
| 2009/0187057 | A1 | 7/2009 | Chewter et al. |
| 2010/0305376 | A1 | 12/2010 | Rothaemel et al. |
| 2011/0112314 | A1* | 5/2011 | Chewter ................ C10G 57/00 585/323 |
| 2012/0271081 | A1 | 10/2012 | Nesterenko et al. |
| 2014/0018593 | A1 | 1/2014 | Birke |
| 2015/0191666 | A1 | 7/2015 | Bradin |
| 2016/0145169 | A1 | 5/2016 | Rothaemel |
| 2016/0312131 | A1 | 10/2016 | Luebke et al. |
| 2017/0121237 | A1 | 5/2017 | Ilias et al. |
| 2018/0155631 | A1 | 6/2018 | O'neill et al. |
| 2018/0155637 | A1 | 6/2018 | Mccarthy et al. |
| 2019/0176136 | A1 | 6/2019 | Beato et al. |
| 2020/0056106 | A1 | 2/2020 | Deimund et al. |
| 2020/0231880 | A1 | 7/2020 | Rajagopalan |
| 2020/0399190 | A1 | 12/2020 | Behkish |
| 2024/0010938 | A1 | 1/2024 | Hidalgo Vivas |
| 2024/0301296 | A1 | 9/2024 | Ingram |

FOREIGN PATENT DOCUMENTS

| | | |
|---|---|---|
| CN | 108970638 A | 12/2018 |
| CN | 110023458 A | 7/2019 |
| CN | 111111765 A | 5/2020 |
| CN | 111558393 A | 8/2020 |
| CN | 113289677 A | 8/2021 |
| EP | 1228166 A1 | 8/2002 |
| EP | 2123736 A1 | 11/2009 |
| EP | 3040324 A1 | 7/2016 |
| WO | 0129152 A1 | 4/2001 |
| WO | 2007135053 A1 | 11/2007 |
| WO | 2010097175 A1 | 9/2010 |
| WO | 2010099885 A1 | 9/2010 |
| WO | 2011071755 A2 | 6/2011 |
| WO | 2011138520 A2 | 11/2011 |
| WO | 2013175204 A1 | 11/2013 |
| WO | 2014008337 A1 | 1/2014 |
| WO | 2018045652 A1 | 3/2018 |
| WO | 2018071905 A1 | 4/2018 |
| WO | 2018106396 A1 | 6/2018 |
| WO | 2018106397 A1 | 6/2018 |
| WO | 2019020513 A1 | 1/2019 |
| WO | 2019158687 A1 | 8/2019 |
| WO | 2019228797 A1 | 12/2019 |
| WO | 2020060591 A1 | 3/2020 |

OTHER PUBLICATIONS

Baerlocher, et al., "Atlas of Zeolite Framework Types", Structure Commission of the International Zeolite Association by Elsevier, Sixth Revised Edition, 2007, 405 pages.
European Search Report dated Feb. 24, 2021, issued by the European Patent Office in corresponding European Application No. 0198386.3-1101. (8 pages).
International Search Report (PCT/ISA/210) and Written Opinion (PCT/ISA/237) mailed on Dec. 10, 2021, by the European Patent Office as the International Searching Authority for International Application No. PCT/EP2021/076369. (16 pages).
International Search Report (PCT/ISA/210) and Written Opinion (PCT/ISA/237) mailed on Dec. 10, 2021, by the European Patent Office as the International Searching Authority for International Application No. PCT/EP2021/076372. (21 pages).
International Search Report (PCT/ISA/210) and Written Opinion (PCT/ISA/237) mailed on Dec. 10, 2021, by the European Patent Office as the International Searching Authority for International Application No. PCT/EP2021/076373, 16 pages.
Search Report mailed on Mar. 25, 2021, by the Danish Patent Office for Application No. PA 2020 01110, 9 pages.
Search Report mailed on Mar. 26, 2021, by the Danish Patent Office for Application No. PA 2020 01109. (9 pages).
Yarulina et al., "Suppression of the Aromatic Cycle in Methanol-to-Olefins Reaction over ZSM-5 by Post-Synthetic Modification Using Calcium", ChemCATChem, 2016, pp. 3057-3063, vol. 8, Issue 19.
Teketel et al., "Co-conversion of methanol and light alkenes over acidic zeolite catalyst H-ZSM-22: Simulated recycle of non-gasoline range products", Applied Catalysis A: General, 2015, pp. 68-76, vol. 494, No. 31.
U.S. Appl. No. 18/849,228, filed Sep. 20, 2024, Finn Joensen.

* cited by examiner

METHANOL TO OLEFIN (MTO) PROCESS

FIELD OF THE INVENTION

The present invention relates to the conversion of a feedstock comprising oxygenates such as methanol and/or dimethyl ether to an olefin stream essentially free of aromatics and ethylene (C2=), yet with a high content of higher olefins C3=-C8=, especially (C4=-C8=) and optionally a significant amount of isoparaffins. The invention relates also to the subsequent conversion of the olefin stream to the hydrocarbons boiling in the jet fuel range, particularly sustainable aviation fuel (SAF), by oligomerization and hydrogenation.

BACKGROUND OF THE INVENTION

Currently, processes for the conversion of oxygenates such as methanol to olefins (MTO) are used to produce ethylene and propylene as the main olefin products with the purpose of serving as feedstock for plastic production. When higher hydrocarbons are the desired product such as in e.g. methanol to gasoline (MTG) processes, around 30% of aromatics are typically formed. However, when producing hydrocarbons boiling in the jet fuel range, particularly sustainable aviation fuels (SAF), current requirements do not allow the presence of aromatics in the olefin stream feed.

Due to society concerns about global climate change and the resulting political pressure on the aviation industries, the market for SAFs is expected to increase substantially during the next decades. Currently, a small number of biocatalytic and thermo-catalytic processes have been approved by ASTM to be able to produce SAFs. Hence, a pre-condition for the use of any SAF as aviation turbine fuel is an ASTM certification. So far, only a small number of processes, producing SAF or synthetic paraffinic kerosene (SPK) fuels have been approved by ASTM International (ASTM) Method D7566 for blending into jet fuel at levels up to 50%. One important general requirement is therefore, that the synthetic part of SAF (50 vol %) must be virtually free from aromatics, while the final SAF blend can contain up to 26.5 vol % aromatics.

So far, the only process that is foreseen to be able to produce relevant amounts of SAF is based on biomass derived Fischer-Tropsch (FT) synthesis, followed by multi-step and cost intensive refining of the FT product, with a moderate final selectivity towards jet-fuel. The present invention uses the well-known methanol to olefins (MTO) process as a more attractive route to obtain olefins at a higher selectivity. Currently, the proposed process layouts for the conversion of methanol to jet fuel are multistep processes, consisting of at least MTO, oligomerization and hydrogenation which are all proven technologies but in combination do not appear very efficient, due to high recycle streams and very different process conditions for the individual steps.

Potential feedstocks for producing SAFs are generally classified as (a) oil-based feedstocks, such as vegetable oils, waste oils, algal oils, and pyrolysis oils; (b) solid-based feedstocks, such as lignocellulosic biomass (including wood products, forestry waste, and agricultural residue) and municipal waste (the organic portion); or (c) gas-based feedstocks, such as biogas and synthesis gas (syngas). Syngas, alcohols, sugars, and bio-oils can be further upgraded to jet fuel via a variety of synthesis, either fermentative or catalytic processes.

There is currently no viable one-step catalyst/process that would allow to convert a feedstock comprising oxygenates such as methanol directly into a hydrocarbon boiling in the jet fuel range, i.e. jet fuel, at least not at reasonable yields. To produce jet fuel starting from methanol, typically a three-step process is used consisting of: a) Methanol to olefins (MTO), b) Oligomerization of olefins, and c) Hydrogenation of long chain olefins. Conventional approaches to the conversion of methanol to gasoline or diesel hydrocarbon products were envisaged already in the late 1970s and early 1980s. Thus, U.S. Pat. Nos. 4,021,502, 4,211,640, 4,227,992, 4,433,185, 4,456,779, disclose process layouts based on classical MTO process conditions, i.e. high temperatures e.g. about 500° C. and moderate pressures e.g. about 1-3 bar, in order to obtain efficient conversion of methanol to olefins. However, under these conditions a significant amount of aromatic hydrocarbons (aromatics) is produced, e.g. 10-30 wt % or 10-35 wt % in the olefin stream, which needs to be separated and a relatively large volume of MTO product effluent has to be cooled and treated to separate a C2-light gas stream, which is unreactive, except for ethene which is reactive to only a small degree. The remaining of the olefin stream has to be pressurized to the substantially higher pressure of the oligomerization (OLI) reactor.

Hence, so-called Mobil-Olefin-to-Gasoline-Distillates (MOLD) process patents from the early 1990s such as U.S. Pat. No. 5,177,279 try to solve these problems and improve the overall operation efficiency by further process integration of MTO and oligomerization and reduce the investment costs by splitting the methanol stream between the MTO and the OLI reactor. The splitting of the methanol feed has two advantages: first it reduces the MTO reactor size at the same overall methanol conversion and secondly only half of the methanol is processed at the high temperature conditions of the MTO reactor, thereby reducing both, the aromatics and the C2-content.

Two possible general process layouts are disclosed in U.S. Pat. No. 5,177,279: (1) classical twostep process with MTO and OLI/MOLD reactor in series and (2) a three-step process, including an intermediate "olefin interconversion" (MOI) reactor that converts the lighter olefins (C2=-C3=) to heavier olefins (C5=-C9=), increasing thereby the amount of higher (heavier) olefins from 25-35 wt % to 35-70 wt %. The latter process design provides more flexibility and only two reactors (MTO+MOI) are used when gasoline is the desired product, while all three reactors are used when distillates are the preferred product.

U.S. Pat. No. 9,957,449 discloses a process for producing hydrocarbons in the jet fuel range by oligomerization of renewable olefins having three to eight carbons.

U.S. Pat. No. 8,524,970 discloses a process for producing diesel of better quality, i.e. diesel with a higher cetane number comprising conversion of oxygenates to olefins, oligomerization of olefins and subsequent hydrogenation.

Yarulina et al, ChemCatChem 8 (2016) 3057-3063, discloses the use of Ca-modified ZSM-5 for methanol to olefins conversion with the purpose of achieving a high propylene selectivity, where the process is conducted at 1 bar and at high temperature of 500° C. The resulting olefin streams shows no formation of aromatics and a high selectivity for light olefins (C2=-C3=), yet low selectivity for higher olefins (C4=-C8=).

US 2002/0103406 A1 discloses a process for dimerizing or oligomerizing an olefin stream using a nickel-based catalyst.

WO 2011/138520 A2, EP 2123736 A1 and WO 2014/008337 A1 disclose variations of processes for producing hydrocarbons including jet fuel by dehydration of an alcohol in the presence of a zeolite, particular ZSM-5, at a wide range of temperatures and pressures to form mainly ethylene. Similarly, US 2018/155637 A1, U.S. Pat. No. 8,524,970 B2 disclose a process for producing an olefin stream from oxygenates over a ZSM-5 catalyst.

US2020/0290940 and US 2020/290940 A1 disclose a process for isomerizing olefins by using ZSM-5, ZSM-23, ZSM-35, ZSM-11, ZSM-12, ZSM-48, ZSM-57 and mixtures or combinations thereof, and wherein the microporous crystalline aluminosilicate has a $SiO_2/Al_2O_3$ molar ratio of less than or equal to about 100.

U.S. Pat. No. 7,482,300 discloses a composition comprising ZSM-48 crystals having a silica:alumina molar ratio of 110 or less, or at least 70, which is free of non-ZSM-48 seed crystals and free of ZSM-50. The composition is used for catalytic dewaxing.

Applicant's US 2019/0176136 discloses the use of a ZSM-23 zeolite as catalyst for methanol to olefin conversion in a process step which is conducted at atmospheric pressure (about 1 bar) and 400° C., thereby producing a hydrocarbon stream with. less than 5 wt % aromatics. The catalyst lifetime is increased by providing the catalyst with particular dimensions in the direction of the channel system.

US 2017/0121237 A1 discloses a process for converting oxygenate containing feedstocks to gasoline and distillates, in which methanol conversion catalysts is selected from a wide range of zeolites, including ZSM-48 and at the conditions of pressure being between 15 and 90 psig and the temperature being above 450° C.

U.S. Pat. No. 4,476,338 discloses a process for converting methanol and/or dimethyl ether to olefins comprising a major fraction of light olefins, at moderate temperature and atmospheric pressure comprising contacting the feed with a crystalline zeolite catalyst designated as ZSM-48. This citation teaches (Ex. 1-2, Table 2) the use of ZSM-48 with a silica-to-alumina ratio (SAR) higher than 110, more specifically 113 or 180, and where methanol is converted over the zeolite catalyst at atmospheric pressure and a moderate temperature of 370° C. There is a significant production of aromatics, in the range 10-12 wt %

SUMMARY OF THE INVENTION

As used herein, "MTO" (methanol to olefins) means the conversion of an oxygenate such as methanol to olefins.

As used herein, "OLI" means oligomerization.

As used herein, "Hydro" means hydrogenation.

As used herein, "Hydro/OLI" means a single combined step comprising hydrogenation and oligomerization.

As used herein, "MTJ" means methanol to jet fuel and is interchangeable with the term "overall process" or "overall process and plant", which means a process/plant combining MTO, OLI and Hydro, whereby a feedstock comprising oxygenates such as methanol is converted into jet fuel.

As used herein, the terms "jet fuel" and "hydrocarbons boiling in the jet fuel range" are used interchangeably and have the meaning of a mixture of C8-C16 hydrocarbons boiling in the range of about 130-300° C. at atmospheric pressure.

As used herein, "SAF" means sustainable aviation fuel or aviation turbine fuel, in compliance with ASTM D7566 and ASTM D4054.

As used herein, the terms "methanol" and "dimethyl ether" are used interchangeably with the terms MeOH and DME, respectively. "MeOH/DME" means MeOH and/or DME.

As used herein, "olefin stream" means a hydrocarbon stream rich in olefins comprising higher and lower olefins, and optionally also aromatics, paraffins, iso-paraffins and naphthenes, and in which the combined content of higher and lower olefins is at least 25 wt %, such as 30 wt % or 50 wt %.

As used herein, the term "higher olefins" means olefins having three (3) or more carbons (C3+ olefins), in particular C3-C8 olefins (C3=-C8=), including olefins having four (4) or more carbons (C4+ olefins), in particular C4-C8 olefins (C4=-C8=).

As used herein, the term "lower olefins" means an olefin having two carbons, i.e. ethylene (C2-olefin or synonymously C2= or ethene).

As used herein, the term "high content of higher olefins" means that the weight ratio in the olefin stream of higher olefins to lower olefins is above 1, suitably above 10, for instance 20-90 such as 70-80.

As used herein, the term "selectivity to higher olefins" means the weight ratio of higher to lower olefins i.e. weight ratio of higher olefins to ethylene. "High selectivity to higher olefins" or "higher selectivity to higher olefins" means a weight ratio of higher to ethylene of above 10.

As used herein, the terms "C2-light fraction" means C2= and C1-2 hydrocarbons.

As used herein, the term "lower hydrocarbons" means C1-2 (e.g. methane, ethane) and optionally also C2=. The term is also used interchangeably with the term "light paraffins".

As used herein, the term "essentially free or ethylene" or "free of ethylene" means 1 wt % or lower.

As used herein, the term "essentially free of aromatics", "substantially free of aromatics", "aromatic-free" or "low aromatics" means less than 5 wt %, e.g. 1 wt % or even less than 1 wt %. Aromatics include benzene (B), toluene (T), xylene (X) and ethylbenzene.

As used herein, the term "partial conversion of the oxygenates" or "partly converting the oxygenates" means a conversion of the oxygenates of 20-80%, for instance 40-80%, or 50-70%.

As used herein, the term "full conversion of the oxygenates" or "fully converting the oxygenates" means above 80% conversion of the oxygenates, for instance 90% or 100%.

As used herein, the term "substantial methanol conversion" is used interchangeably with the term "full conversion of the oxygenates", where the oxygenate is methanol.

As used herein, the terms "catalyst comprising a zeolite" and "zeolite catalyst" are used interchangeably.

As used herein, the term "silica to alumina ratio (SAR)" means the mole ratio of $SiO_2$ to $Al_2O_3$.

As used herein, the term "significant amount of paraffins" means 5-20 wt %, such as 10-15 wt % in the olefin stream.

It is an object of the present invention to provide a process for the conversion of oxygenates such as methanol to olefins (MTO), that is capable of producing a more efficient olefin stream as feed for oligomerization, in particular an olefin stream (olefin feed for oligomerization) having low aromatics, high content of higher olefins, being essentially free of ethylene and optionally having a significant amount of isoparaffins.

It is another object of the present invention to provide such an olefin feed for oligomerization while still maintaining full conversion of the oxygenates.

It is yet another object of the present invention to be able to achieve any of the above objects while also being able to increase the longevity of the catalyst, while conducting the oxygenate conversion to olefins.

These and other objects are solved by the present invention.

Accordingly, in a first aspect the present invention is a process for producing an olefin stream, said process comprising: passing a feedstock stream comprising oxygenates over a catalyst active in the conversion of oxygenates, in which the catalyst comprises a zeolite with a framework having a 10-ring pore structure, in which said 10-ring pore structure comprises a unidimensional (1-D) pore structure, at a pressure of 1-25 bar such as 2-25 bar or 1-15 bar, and a temperature of 240-360° C. such as 260-360° C. or 300-360° C. for instance 300-340° C.; and wherein said 1-D pore structure is any of *MRE (ZSM-48), MTT (ZSM-23), TON (ZSM-22), or combinations thereof.

A zeolite with a framework having a 10-ring pore structure means a pore circumference defined by 10 oxygens.

A 1-D pore structure means zeolites containing non-intersecting pores that are substantially parallel to one of the axes of the crystal. The pores preferably extend through the zeolite crystal.

The three letter code, e.g. *MRE, for structure types are assigned and maintained by the International Zeolite Association Structure Commission in the Atlas of Zeolite Framework Types, which is at http://www.iza-structure.org/databases/or for instance also as defined in "Atlas of Zeolite Framework Types", by Ch. Baerlocher, L. B. McCusker and D. H. Olson, Sixth Revised Edition 2007.

It would be understood that the term "ZSM-48" may be used interchangeably with the term "EU-2".

It would be understood that the term "temperature" means the MTO reaction temperature in an isothermal process, or the inlet temperature to the MTO in an adiabatic process.

In an embodiment, the catalyst comprises a binder. The catalyst is suitably formed by combining the zeolite with the binder, and then forming the catalyst into pellets. The pellets may optionally be treated with a phosphoric reagent to create a zeolite having a phosphorous component between 0.5 and 15 wt % of the treated catalyst i.e. 0.5-15 wt % phosphorous in the catalyst. The phosphorous provides stability to the catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

In an embodiment, the catalyst contains up to 30-90 wt % zeolite with the binder, suitably 50-80 wt %, the binder suitably comprising an alumina component such as a silica-alumina. For instance, the process comprises mixing e.g. impregnating the catalyst with the binder, such that the catalyst contains up to said 50-80 wt % zeolite with the binder, the binder suitably comprising an alumina component such as a silica-alumina, thus forming a silica-alumina binder. As an example, the catalyst is 60 wt % zeolite and 40 wt % alumina.

It would be understood that the wt % of zeolite in the binder means the wt % of the zeolite with respect to the catalyst weight, in which the catalyst comprises the zeolite and the binder.

It would also be understood, that for the purposes of the present application, the term "binder" is also referred to as "matrix binder" or "matrix/binder" or "binder/matrix".

The binder confers hardness and strength of the catalyst. However, it has now been found that the use of a binder in the catalyst comprising an alumina component, also conveys the undesired effect of MeOH/DME-cracking in the MTO when operating at temperatures above 360° C., thereby producing methane as an undesired by-product. The methane needs to be disposed of, e.g. by burning or flaring, which increases the carbon footprint of the process and plant. Further, the yield of the desired olefin stream (olefin product stream) comprising i.a. higher olefins is reduced, as some of the feed is converted to the undesired methane by-product instead. It would be understood, that in the MTO reaction, methanol may be initially converted to DME by methanol dehydration.

Hence, now surprisingly, it turns out that the binder of the catalyst at the low MTO temperatures of the present invention (360° C. or below), does not promote MeOH/DME cracking so the undesired methane is not produced, thereby enabling an increase in yield of the desired olefin stream as explained above. Without being bound by any theory, it is believed that by the present invention, the DME quickly reacts to olefins before cracking into methane.

The invention provides thereby the benefits associated to having a binder, incl. better stability of the catalyst, while at the same time eliminating its disadvantages, namely the promotion of MeOH/DME cracking into undesired methane.

In an embodiment, the zeolite has a silica-to-alumina ratio (SAR) of up to 240. In a particular embodiment, the zeolite has a SAR of up to 110, such as up to 100. In another particular embodiment, the zeolite has a SAR is higher than 10, for instance 15 or 20, or 30, 40, 50, 60, 70, 80, 90, 100.

In typical MTO, normally operating at above 360° C. and using a ZSM-5 zeolite in the catalyst, the lifetime of the catalyst is proportional to the SAR, thus higher SAR values enable a longer catalyst lifetime, which is desirable for MTO operation. However, high SAR values e.g. 120 or higher, convey also the penalty of a reduction in catalytic activity. Hence, the higher activities of the catalyst are found at lower SAR values, which then reduces the catalyst lifetime. By the present invention, it turns out that the catalyst lifetime is inversely proportional to the SAR, thus lower SAR values e.g. 110 or lower as recited above, result in a longer catalyst lifetime, yet at the same time there is no penalty being incurred in terms of reduction in catalytic activity.

In an embodiment, the pressure is 2-25 bar, such as 2, 5, 10 or 12 or 17 or 20 or 22 bar. It has been found that while higher pressures—above 25 bar—increase the ratio of higher olefins to lower olefins i.e. higher selectivity to higher olefins, the higher pressures may also decrease the total yield of olefins, i.e. lower conversion of the oxygenate feed to olefins and also increase the required temperature to achieve full conversion, and which in turn may create the risk of less desired cracking reactions taking place. At the pressure range recited above, for instance 2-10 bar, 5-10 bar, 1-15 bar, or 20-25 bar, it is now possible to obtain a higher selectivity to higher olefins without requiring increasing the temperatures to high levels for achieving full conversion, thereby also reducing the occurrence of cracking reactions. Further, the formation of ethylene is suppressed and so is the formation of aromatics. The olefin stream, therefore, contains the higher olefins C3-C8 as well as isoparaffins. In particular, conducting the process at higher pressures than atmospheric have the effect of enabling an amount of diluent as "heat sink" for the exothermal reaction. See also below in connection with for instance the particular embodiment directed to the feedstock stream being combined with a diluent, where the feedstock stream is e.g. methanol and it is diluted to a methanol concentration in the feedstock of 2-20 vol. %, preferably 5-10 vol. %.

Hence, in an embodiment, the feedstock stream is combined with a diluent, i.e. an inert diluent, such as nitrogen or carbon dioxide or a light paraffin such as methane, thereby reducing the exothermicity in the conversion to olefins, which is particularly preferred when the catalyst is arranged as a fixed bed. For instance, where the feedstock stream is methanol, it is diluted with e.g. nitrogen so that the methanol concentration in the feedstock is 2-20 vol. %, preferably 5-10 vol. %.

It would be understood that the lower the methanol concentration in the feedstock, the higher the pressure which is required to maintain high methanol conversion, since the partial pressure of methanol ($P_{MeOH}$), is the actual relevant parameter to track during operation of the process. For instance, where the concentration of methanol in the feedstock is 10 vol. %, and the MTO is operated at a $P_{MeOH}$ of 0.3 or 0.5 bar, this corresponds to the pressure in the MTO being 3 or 5 bar, respectively. If the concentration of methanol in the feedstock is 5 vol. %, and the MTO is operated at a $P_{MeOH}$ of 0.3 or 0.5 bar, this corresponds to the pressure in the MTO being 6 or 10 bar.

A pressure at the higher end of the range, e.g. 15 bar, 20 bar or 25 bar, enables better match—and thereby significant compression energy savings—with the pressure of a subsequent oligomerization or Hydro/OLI, as also explained farther below. The invention provides, therefore, also a process whereby it is now possible to closely match the pressure of the MTO with the pressure of the subsequent oligomerization or Hydro/OLI, while still maintaining high conversion and an olefin stream (olefin product stream) which is ideal for subsequent oligomerization and/or Hydro/OLI.

It has now also been found, that at the low temperatures of the MTO according to the present invention, the partial pressures of the feed, e.g. methanol ($P_{MeOH}$), do not play a decisive role in terms of selectivity to aromatics. This is contrary to the common understanding that methanol partial pressures play a decisive role in the selectivity to aromatics and paraffins. This means, that compared with operation of the MTO at temperatures higher than 360° C., where $P_{MeOH}$ has a high effect on the amount of aromatics produced, with higher $P_{MeOH}$ significantly generating higher content of aromatics; by the present invention where operation of the MTO is conducted at temperatures of 360° C. or below, e.g. 320° C., changing the $P_{MeOH}$ does not show any significant influence, as the content of aromatics is maintained below 2 wt % or below 1 wt % and at similar values regardless of the $P_{MeOH}$.

For instance, with MTO operating at 400° C., at $P_{MeOH}$ of 0.3 and 0.5 the content of aromatics is about 2 wt % and 6 wt %, respectively. When operating the MTO at 360° C., at $P_{MeOH}$ of 0.3 and 0.5 the content of aromatics is about 1 wt % and 2 wt %, respectively. When operating the MTO at 320° C., at $P_{MeOH}$ of 0.3 and 0.5 the content of aromatics is about 1 wt % at both $P_{MeOH}$.

Thus, the higher the $P_{MeOH}$, the higher the content of aromatics. By reducing the temperature according to the present invention, it is possible to increase the $P_{MeOH}$ to some degree and thereby the pressure (total pressure), without producing more aromatics.

Hence, by the present invention, the higher independence of the aromatic content with respect to $P_{MeOH}$ at the lower MTO temperatures, for instance at temperatures of 350° C. or below, such as 340° C. or 320° C. or 300° C., enables also operation at the higher end of the pressures, e.g. 15, 20 or 25 bar. Not only are these pressures better matched to the downstream operations, e.g. oligomerization or Hydro/OLI, as mentioned above, but they are also closer to the pressures used in the upstream process, in particular methanol synthesis, which operates at high pressures, typically about 50-100 bar. Higher energy savings in terms of lower compression energy is thereby achieved, as so is a reduction in equipment size.

Despite the relatively low temperatures used, i.e. reaction temperatures of 240-360° C. e.g. 260-360° C., or 260-340° C., the catalysts are also active in not only suppressing the formation of aromatics, but also in providing a high selectivity for the higher olefins C3=-C8=, no ethylene formation, significant isoparaffin formation, full conversion, while also showing an extended catalyst lifetime.

For instance, it has been found that ZSM-48, when applied at said low temperatures, converts methanol to an olefin stream which is ideal for further oligomerization to jet fuel, particularly SAF in accordance with ASTM as defined above. The fact that the olefin product is essentially free of ethylene and aromatics, which are considered unwanted, while the yield of C3-C8 olefins is between 70-80%, combined with 10-15% isoparaffins, makes the product an ideal feed for further oligomerization to SAF.

Compared with the prior art according to U.S. Pat. No. 4,476,338, where MTO is conducted over a ZSM-48 having SAR of 113 or 180 and at 370° C. (Example 1 and 2 therein), in the present invention, where MTO is conducted at temperatures of 360° C. or below with a ZSM-48 having e.g. a lower SAR, there is a higher production of total olefins (e.g. C2-C8 olefins); lower production of ethylene, for instance the content of ethylene now being less than 1 wt %; lower production of aromatics, for instance the content of aromatic compounds now being less than 1 wt %; and optionally higher production of isoparaffins, for instance now 10-15 wt %. Furthermore, the lifetime of the catalyst is increased, as explained below.

The combination of operating the oxygenate conversion with e.g. ZSM-48 with SAR up to 110 and lower temperature (300-360° C.) conveys at least three highly beneficial effects:

a) the selectivity to ethylene and aromatics is decreased to below 1 wt % in either case.

b) a significant amount of isoparaffins may be formed, which can be used in the process. Isoparaffins, as well as the C3-C8 olefins, may also be oligomerized, so that isoparaffins may be formed as a desired by-product. The isoparaffins may optionally be separated for alkylation to increase octane number and then be incorporated into a gasoline pool, or simply be used as part of the olefin stream for downstream oligomerization.

c) due to the lower applicable temperature, the overall lifetime (number of cycles) of the catalyst is increased as an effect of the lower dealumination rate (affected by the combination of high temperature and water vapor produced during reaction). Further, the lifetime during each cycle, i.e. cycle time, of the catalyst is substantially increased, which without being bound by any theory, is probably an effect of the lower selectivity to aromatics due to less hydrogen transfer reactions. High catalyst longevity in terms of both overall lifetime (number of cycles) and cycle time, is highly important for enabling its use in actual commercial applications.

For the purposes of the present application, the terms "catalyst longevity" and "catalyst lifetime" are used interchangeably.

Moreover, if a binder is included in the catalyst, which is relevant for commercial applications, the present invention will also enable a higher yield of desired products, e.g. C3-C8 olefins, since no or limited MeOH/DME cracking to methane occurs.

Accordingly, the features of the invention cooperate synergistically to bring about a superior process which is commercially applicable for conversion of the oxygenates to olefins and thereby for the subsequent downstream steps, e.g. oligomerization.

While a suitable oligomerization feed may normally have some aromatics, for instance 10-20 wt % aromatics, as well as higher olefins and ethylene, the ideal oligomerization feed is namely substantially free of aromatics and composed of higher olefins, and preferably as little as possible C2-light fraction, more particularly, free of ethylene. The olefin stream may comprise at least 70 wt % C3-C8 olefins, such as 75-85 wt % C3-C8 olefins e.g. 80 wt % C3-C8 olefins, 1 wt % or less of aromatics, 1 wt % or less of ethylene, and 10-15 wt % isoparaffins. The lower the temperature, the higher the content of higher olefins and thereby also the ratio of higher olefins to ethylene, i.e. the selectivity to higher olefins. Also, the lower the temperature, the lower the content of ethylene so the olefin stream is essentially ethylene-free, while the content of isoparaffins increases. Thus, the oligomerization feed complies with the above ASTM requirements stipulating the 50% SAF blending part to be almost aromatic-free, more specifically that the content of aromatics be limited to below 0.5 wt %. The olefin stream can be converted into such jet fuel via oligomerization and hydrogenation in a more efficient overall process due to i.a. less recycling and higher oligomerization yields. In other words, the higher olefins and low selectivity to aromatics and ethylene simplifies separation steps and increase overall yields of the jet fuel.

By using the moderately high pressure of 2-25 bar, for instance 2,10, 15 or 20 bar, it is now possible to further shift the selectivity towards higher olefins. It has namely been found that while higher pressures increase the ratio of higher olefins to lower olefins i.e. higher selectivity to higher olefins, the higher pressures may also decrease the total yield of olefins (i.e. lower conversion of the oxygenate feed to olefins) and also increase the required temperature to achieve full conversion, which in turn creates the risk of less desired cracking reactions taking place. At the pressure range of 1-25 bar, it is now possible to obtain a higher selectivity to higher olefins without requiring increasing the temperatures to e.g. above 360° C. for achieving full conversion, thereby also reducing the occurrence of cracking reactions. By conducting the process at pressure above 1 bar, e.g. 2 bar or higher, it is also possible to provide an amount of diluent "heat sink" for the exothermal reaction, as explained farther above. The invention enables a high flexibility in the selection of pressures, for instance at the higher end of the pressure range, such as 20 or 25 bar, as also explained farther above.

At the same time, reducing the temperature to for instance 300° C. or 320° C. or lower, despite this in principle implying a reduction in methanol conversion, in fact still maintains the oxygenate conversion at close to 100%, while at the same time maintaining the content of aromatics below 1 wt % as well the content of ethylene below 1 wt %.

The catalysts may be prepared by standard methods in the art, for instance as disclosed in U.S. Pat. No. 4,476,338 for ZSM-48. Suitably, there is mixing of the final catalyst with a binder/matrix, such as in a catalyst that contains up to 50-80 wt % zeolite in a matrix/binder comprising an alumina component such as a silica-alumina matrix binder.

In an embodiment, the process further comprises recycling a portion of an olefin containing stream to the feedstock stream, said portion of the olefin containing stream suitably being a stream comprising C2-C3 olefins or a C3 olefin stream (propylene stream) which is withdrawn from said olefin stream.

In other words, the process further comprises recycling a portion of the olefin stream to the feedstock stream and using it as additional feed stream, i.e. as a co-feed, and which may include recycling light paraffins, including methane, acting as a diluent, and reducing the adiabatic temperature increase, e.g. by combining with the feedstock stream comprising oxygenates. Thereby it is possible to further reduce the operating temperature of the oxygenate conversion and thereby improve both selectivity and catalyst lifetime.

The concentration of higher olefins in the olefin stream is further increased while also having full utilization of the less desired lower olefins for conversion into higher olefins. Any undesired cracking of higher olefins in the process is contained by recycling products of such cracking, namely C2-C3 olefins, back to the feed. Furthermore, this recycle, suitably also containing light paraffins and optionally also isoparaffins, further provides a dilution effect on the feedstock stream, thereby enabling better control of the exothermicity during the conversion to olefins.

The co-feed stream, i.e. the recycle stream, is between 1 to 20 times, such as 2 to 10 times, the volumetric amount of the feedstock stream e.g. methanol feed stream.

In a particular embodiment, the recycle stream contains is 0.5-10% or 1-10% mol propylene and the concentration of methanol in the feed is 10 vol. %.

In particular, it has now been found that:

Co-feeding the lower (light) olefins, such as C3-olefins, enables the initiation of the MTO at lower temperatures. Hence, a further reduction in temperature is possible, for instance 350, 340, 320 or 300° C. or, under adiabatic conditions, even lower, 280 or 260 or even 240° C. This conveys the benefit of further reduction in hydrogen transfer and thereby less production of paraffins, isomers and aromatic compounds, yet providing a higher olefin chain length i.e. higher olefins, as well as more freedom with respect to the total (or methanol partial) pressure; for instance, the pressure may be increased, which as mentioned above may be advantageous.

Further, it has surprisingly been found that there is also a dramatic increase in catalyst longevity when providing the co-feed compared to when there is no co-feed i.e. by using a neat methanol feed.

It would be understood that the term "catalyst longevity" or "catalyst lifetime" comprises not only overall lifetime of the catalyst (number of cycles), but also the lifetime during each cycle, i.e. cycle time. The term "cycle time", also known as "cycle length" is the length of the period where the catalyst exhibits proper catalytic activity, and which is typically measured as hours-on-stream (HOS). From a process point of view this is highly beneficial, since the recycle stream of C2-C3 olefins will also enable easier control of the exothermicity of the MTO.

In an embodiment, the weight hour space velocity (WHSV) is 0.1-3 h$^{-1}$, such as 1-2 h$^{-1}$. At higher values of WHSV, the methanol conversion becomes too low.

In an embodiment, the feedstock stream comprising oxygenates is derived from one or more oxygenates taken from the group consisting of triglycerides, fatty acids, resin acids, ketones, aldehydes or alcohols or ethers, where said oxygenates originate from one or more of a biological source, a gasification process, a pyrolysis process, Fischer Tropsch synthesis, or methanol-based synthesis. In a particular embodiment, said one or more oxygenates are hydroprocessed oxygenates. By "hydroprocessed oxygenates" is meant oxygenates such as esters and fatty acids derived from hydroprocessing steps such as hydrotreating and hydrocracking.

In an embodiment, the oxygenates are selected from methanol (MeOH), dimethyl ether (DME), or combinations thereof. These are particularly advantageous oxygenate feedstocks, as these are widely commercially available. DME is more reactive than methanol and thus enables running the MTO step at lower temperatures, thereby increasing the selectivity for higher olefins. Furthermore, conversion of DME, releases only half the amount of water (steam) compared to methanol, thereby reducing the rate of (irreversible) deactivation due to steam-dealumination of the zeolite catalyst.

Suitably, water is removed from the olefin stream produced in the MTO, since its presence may be undesirable when conducting the downstream oligomerization.

In an embodiment, the methanol is made from synthesis gas, i.e. methanol synthesis gas, prepared by using electricity from renewable sources such as wind or solar energy, e.g. eMethanol™. Hence, in an embodiment, the synthesis gas is suitably prepared by combining air separation, autothermal reforming or partial oxidation, and electrolysis of water, as disclosed in Applicant's WO 2019/020513 A1, or from a synthesis gas produced via electrically heated reforming as for instance disclosed in Applicant's WO 2019/228797. Thereby, an even more sustainable approach for the production of jet fuel, in particular SAF, is achieved. Methanol can be produced from many primary resources (including biomass and waste), in times of low wind and solar electricity costs, the production of E-Methanol™ enables an even more sustainable front-end solution.

In a particular embodiment, the process of the invention further comprises, prior to passing the feedstock stream comprising oxygenates over a catalyst active in the conversion of oxygenates, in which the feedstock comprising oxygenates is a methanol stream i.e. methanol feed stream:

produce said methanol feed stream by methanol synthesis of a methanol synthesis gas, wherein the methanol synthesis gas is generated by: steam reforming of a hydrocarbon feed such as natural gas, and/or at least partly by electrolysis of water and/or steam.

Hence, in another particular embodiment, the methanol feed stream is produced from methanol synthesis gas which is generated by combining the use of water electrolysis in an alkaline or PEM electrolysis unit, or steam in a solid oxide electrolysis cell (SOEC) unit, thereby generating a hydrogen stream, together with the use of a $CO_2$-rich stream in a SOEC unit for generating a stream comprising carbon monoxide and carbon dioxide, then combining the hydrogen stream and the stream comprising carbon monoxide and carbon dioxide for generating said methanol synthesis gas, as e.g. disclosed in Applicant's co-pending European patent application No. 20216617.9. The methanol synthesis gas is then converted into the methanol feed stream via a methanol synthesis reactor, as is well-known in the art.

The methanol synthesis gas, as is also well-known in the art, is a mixture comprising mainly hydrogen and carbon monoxide tailored for methanol synthesis i.e. by the methanol synthesis gas having a module $M=(H_2—CO_2)/(CO+CO_2)$. The methanol synthesis gas used for the methanol synthesis is normally described in terms of said module M, since the synthesis gas is in balance for the methanol reaction when M=2.

Thereby, an alternative highly sustainable front-end solution for generating the methanol feed stream, i.e. methanol synthesis gas, is provided, whereby only electrolysis is utilized for generating the methanol synthesis gas and thereby the methanol.

It would thus be understood, that as used herein, the term "process" may also encompass the prior (front-end) production of the methanol feed stream, as recited above.

In an embodiment, the catalyst is contacted with a hydrogen stream. The hydrogen may improve the methanol conversion by at least slightly decreasing the rate of deactivation of the catalyst, thereby increasing catalyst lifetime. Yet, when conducting the process, there is no addition of hydrogen, since this conveys a risk of hydrogenating some olefins and thereby decrease the olefin yield.

In an embodiment, the catalyst is arranged as a fixed bed.

In an embodiment, the process comprises: using a first reactor set including a single reactor or several reactors, preferably mutually arranged in parallel, for the partial or full conversion of the oxygenates. Thereby, large feedstocks comprising one or more oxygenates can be handled simultaneously.

It would be understood, that the term "mutually" means in between the reactors of a reactor set, e.g. arranged in parallel in between the reactors of the first reactor set.

In a particular embodiment, the process further comprises using a second reactor set including a single reactor or several reactors, preferably mutually arranged in parallel, for the further conversion of the oxygenates, and a phase separation stage in between the first reactor set and the second reactor set for thereby forming the olefin stream.

As used herein, the term "using a first reactor set" means passing the feedstock comprising oxygenates through the first reactor set. As used herein, the term "using a second reactor set" means passing the feedstock or a portion thereof through the second reactor set after the partial or full conversion of the oxygenates and passage through the separation stage.

Thereby, large feedstocks comprising one or more oxygenates can be handled simultaneously and lower temperatures may be used in both reactor sets, which improves the lifetime conversion capacity of the catalyst and also improves the selectivity to higher olefins due to less cracking.

In an embodiment, the entire feedstock stream passes through the first reactor set, i.e. there is no substantial splitting of the feedstock stream.

As used herein, the term "entire feedstock" means at least 90 wt % of the feedstock.

In another particular embodiment, the process comprises:
passing the feedstock stream comprising oxygenates through the first reactor set under conditions for partly converting, e.g. 40-80% such as 60-70% conversion, the oxygenates, thereby forming a raw olefin stream comprising unconverted oxygenates and C2-C8 olefins, e.g. the raw olefin stream may comprise water, methanol and C2-C8 olefins;

passing the raw olefin stream through said phase separation stage, for producing: a first olefin stream, which is rich in lower olefins;

a separated oxygenate stream comprising the unconverted oxygenates, e.g. the separated oxygenate stream may comprise water and methanol;

a second olefin stream, which is rich in higher olefins;

combining the first olefin stream with the separated oxygenate stream comprising the unconverted oxygenates, thereby forming a combined stream comprising lower olefins and the unconverted oxygenates;

passing the resulting combined stream comprising lower olefins and unconverted oxygenates through the second reactor set, e.g. to the first reactor of the second reactor set, under conditions for fully converting, e.g. 85%, 90%, 95% or higher, the unconverted oxygenates and the lower olefins, into a third olefin stream which is rich in higher olefins;

combining the second olefin stream (which may be regarded as a by-pass stream of the second reactor set) with the third olefin stream, thereby forming said olefin stream, which preferably is rich in higher olefins and substantially free of aromatics.

For instance, the olefin stream, i.e. olefin product stream, contains less than 1 wt % aromatics. The olefin stream is suitably also free of ethylene e.g. less than 1 wt %, while having a significant content of isoparaffins e.g. 10-15 wt %.

Thereby, increased flexibility in operation is achieved, particularly when handling large feedstock streams, without needing to e.g. divide the feedstock stream prior to entering a first reactor for conversion of oxygenates and pass it to a separate olefin interconversion reactor, as for instance disclosed in U.S. Pat. No. 5,177,279. Furthermore, the temperatures in all reactor sets can be lowered even further, for instance down to 250-350° C., yet still achieving full conversion, e.g. up to 100% conversion of the oxygenates. In addition, further lowering the temperature increases also catalyst lifetime. Moreover, there is increased flexibility in the handling of a variety of feedstocks comprising oxygenates, including fatty acids in renewable feeds, or oxygenates originating from one or more of a biological source, as well as the handling of, optionally, different types in catalysts in the two different sets of reactors.

In another particular embodiment, the first reactor and second reactor set use a catalyst having a unidimensional (1-D) pore structure, such as *MRE, for instance ZSM-48. The recycle of C2-C3 olefins as a co-feed may also be conducted. For instance, in an embodiment, the process further comprises recycling a portion of the olefin stream, i.e. the olefin product stream from the second reactor set, to said combined stream comprising lower olefins and the unconverted oxygenates and which is fed to the second reactor set, said portion of the olefin stream preferably being an olefin stream comprising C2-C3 olefins, more preferably a C3-olefin stream, which is withdrawn from said olefin stream. The same associated benefits recited above in connection with the recycling C2-C3 olefins are also obtained.

In another particular embodiment, the first reactor set consists of 2-4 reactors, such as 3 reactors, and the second reactor set consists of 1-3 reactors, such as 2 reactors.

In the first and second reactor set, the reactors are preferably mutually arranged in parallel. In large MTO plants handling large feedstock streams, normally several reactors are run in parallel, e.g. five (5) reactors. By the present invention it is possible to replace the 5 reactors in parallel by for instance the first reactor set consisting of three reactors, and the second reactor set consisting of two reactors. Thereby it is possible to run at full conversion by operating the first three reactors at e.g. only 70% conversion, and then further convert the unconverted oxygenates, e.g. methanol, together the C2-C3 olefins, to 100% in two reactors arranged in series to the first three. Again, the temperature in all five reactors is lowered, yet full conversion is achieved. Flexibility is also improved, by enabling that one reactor may be taken out of service for regeneration.

It would be understood that the first reactor set and second reactor set are arranged in series.

In another particular embodiment, a reactor in the first reactor set and second reactor set operates at 1-25 bar, such as 1-15 bar or 2-25 bar, and at 240-360° C. such as 300-360° C. e.g. 320° C. or 340° C.

In another particular embodiment, the weight hour space velocity (WHSV) is 0.1-3 $h^{-1}$, such as 1-2 $h^{-1}$, for instance 6, 8, or 10 h–1. In yet another particular embodiment, the weight hour space velocity (WHSV) in the first reactor set is higher than in the second reactor set. For instance, in the first reactor set where partial conversion of the oxygenate feedstock is intended, the WHSV is suitably 3 $h^{-1}$ or 6 $h^{-1}$ while in the second reactor set where full conversion is intended the WHSV is suitably 2 $h^{-1}$.

In an embodiment, the process further comprises:
separating from the olefin stream an isoparaffin stream.

In an embodiment, the process further comprises:
passing at least a portion of the olefin stream, e.g. after separating said isoparaffin stream, through an oligomerization step over an oligomerization catalyst, and optionally subsequently conducting a separation step, for thereby producing an oligomerized stream.

The isoparaffins, as well as the C3-C8 olefins, may also be oligomerized. Hence, the invention enables in a way, that instead of having unwanted aromatics as byproduct, isoparaffins are now provided as a desired product, which may optionally be separated for use as alkylation feed to increase octane number of gasoline optionally also produced in the process. The provision of the isoparaffin stream separation step increases also flexibility in the selection of zeolites structures used in the oligomerization step.

In an embodiment, the entire olefin stream passes through the oligomerization step, preferably after said olefin stream comprising C2-C3 olefins is withdrawn from the olefin stream. As used herein, the term "entire olefin stream" means at least 90 wt % of the stream.

In an embodiment, the olefin stream, e.g. the entire olefin stream after separating said isoparaffin stream, is passed directly to the oligomerization step, i.e. the olefin stream is in direct fluid communication with the oligomerization step, or combined oligomerization and hydrogen step, as explained farther below. Thereby, there is no fractionation of the olefin stream prior to entering the oligomerization step, thus further simplifying the process and plant.

The oligomerization step is preferably conducted by conventional methods including the use of an oligomerization catalyst such as solid phosphoric acid ("SPA"), ion-exchange resins or a zeolite catalyst, for instance a conventional *MRE, BEA, FAU, MTT, TON, MFI and MTW catalyst, at a pressure of 30-100 bar, such as 50-100 bar, and a temperature of 100-350° C. The products from the oligomerization reaction may be subsequently separated in the separation step, such as distillation, thereby withdrawing a lighter hydrocarbon stream such as naphtha, which comprises C5-C7 hydrocarbons, and the oligomerized stream, which comprises C8+ hydrocarbons.

In an embodiment, the process further comprises:
passing at least a portion of the oligomerized stream through a hydrogenation step over a hydrogenation catalyst, and optionally subsequently conducting a separation step, for thereby producing a hydrocarbon stream comprising hydrocarbons boiling in the jet fuel range.

The hydrogenation step is preferably conducted by conventional methods, including under the presence of hydrogen the use of a hydrotreating or hydrogenation catalyst, for instance a catalyst comprising one or more metals, e.g. Pd, Rh, Ru, Pt, Ir, Re, Co, Mo, Ni, W or combinations thereof, at a pressure of 60-70 bar and a temperature of 50-350° C. The C8+ hydrocarbons of the oligomerized stream are thereby saturated to form the corresponding paraffins. These may be subsequently separated in a separation step, for instance a distillation step, whereby any hydrocarbons boiling in the diesel range are withdrawn and thereby separated from the hydrocarbons boiling in the jet fuel range i.e. jet fuel.

In an embodiment, the entire oligomerized stream passes through the hydrogenation step. As used herein, the term "entire oligomerized stream" means at least 90 wt % of the stream.

In a particular embodiment, the hydrocarbon stream comprising hydrocarbons boiling in the jet fuel range is SAF, i.e. a sustainable aviation fuel in compliance with ASTM D7566 and ASTM D4054.

In an embodiment of the invention, the oligomerization step and hydrogenation step are combined in a single hydro-oligomerization step (Hydro-OLI), e.g. by combining the steps in a single reactor. In other words, by passing at least a portion of the olefin stream trough an oligomerization step and hydrogenation step which are combined in a single hydro-oligomerization step, and optionally subsequently conducting a separation step, for thereby producing a hydrocarbon stream comprising said hydrocarbons boiling in the jet fuel range. This results in a much simpler process/plant layout.

As used herein, the term "single hydro-oligomerization step" or more generally "single step" or "single stage" means a section of the process in which no stream is withdrawn. Typically, a single stage does not include equipment such as compressors, by which the pressure is increased.

The oligomerization step is dimerization, optionally also trimerization, i.e. by conducting the oligomerization at conditions suitable for dimerization and/or trimerization. Thereby the single reactor is preferably operated at a relatively low pressure, such as 15-60 bar, for instance 20-40 bar. The oligomerization reaction is very exothermic per oligomerization step and much less heat is produced, since there is only dimerization, optionally also trimerization-, instead of higher oligomerization such as tetramerization or even pentamerization. The lower heat produced favors approaching equilibrium, i.e. higher conversion of olefins.

Normally, the oligomerization step converts the olefins to a mixture of mainly dimers, trimers and tetramers or even pentamers; for instance, a C6-olefin will result in a mixture comprising C12, C18, C24 products and probably also higher hydrocarbons. By conducting the oligomerization step at conditions suitable for dimerization, optionally also trimerization, a more selective and direct conversion of the higher olefins (C3-C8 olefins incl. C4-C8 olefins) to the jet fuel relevant hydrocarbons, namely C8-C16, is obtained. The dimerization and optional trimerization step comprises the use of lower pressures than in conventional oligomerization processes, thereby also reducing compression requirements which translates into higher energy efficiency—due to lower compression energy—as well as reduced costs, e.g. reduced costs of the oligomerization reactor and attendant equipment, as well as reduced operating costs due to less need of separating C16+ olefins otherwise formed in conventional OLI reactors. Accordingly, the pressure of the Hydro/OLI can be adapted to better match the pressure of the previous oxygenate conversion step.

Moreover, instead of using a dedicated separation such as distillation in the OLI step for separating naphtha (which can be upgraded to a gasoline product) and another dedicated separation in the hydrogenation step for separating diesel from the jet fuel, only one subsequent separation stage, if any, will be needed. Thereby a simpler process for oligomerization and hydrogenation is obtained and consequently also a simpler overall process and plant.

The hydrogenation or $H_2$-addition is conducted in the same reactor, for instance by adjusting the activity of the hydrogenation component e.g. nickel. In an embodiment, the single hydro-oligomerization step is conducted in a single reactor having a stacked reactor bed where a first bed comprises an oligomerization catalyst, e.g. zeolite catalyst, and a subsequent bed comprises a hydrogenation catalyst.

The hydro-oligomerization step is conducted by reacting, under the presence of hydrogen, the olefin stream, e.g. after separating said isoparaffin stream, over a catalyst comprising a zeolite and a hydrogenation metal, such as a hydrogenation metal selected from Pd, Rh, Ru, Pt, Ir, Re, Co, Cu, Mo, Ni, W and combinations thereof, and preferably at a pressure of 15-60 bar such as 20-40 bar, and a temperature of 50-350° C., such as 100-250° C. In a particular embodiment, the catalyst comprises a zeolite having a structure selected from MFI, MEL, SZR, SVR, ITH, IMF, TUN, FER, EUO, MSE, *MRE, MWW, TON, MTT, FAU, AFO, AEL, and combinations thereof, preferably a zeolite with a framework having a 10-ring pore structure i.e. pore circumference defined by 10 oxygens, such as zeolites having a structure selected from TON, MTT, MFI, *MRE, MEL, AFO, AEL, EUO, FER, and combinations thereof. These zeolites are particularly suitable due to the restricted space of the zeolite pores, thereby enabling that the dimerization is favored over larger molecules. Optionally, the weight hour space velocity (WHSV) is 0.5-6 $h^{-1}$, such as 0.5-4 $h^{-1}$.

Lower pressures corresponding to the operating at conditions for dimerization, optionally also trimerization, are in particular 15-50 bar, such as 20-40 bar. This, again, is significantly lower than the pressures normally used in oligomerization, which typically are in the range 50-100 bar.

The present invention purposefully uses conditions that result in a mild hydrogenation. Particularly suitable catalysts are catalysts comprising NiW, for instance sulfide NiW (NiWS), or Ni such as Ni supported on a zeolite having a FAU or MTT structure, for instance a Y-zeolite, or ZSM-23. The catalyst which is active for oligomerization and hydrogenation may for instance contain up to 50-80 wt % zeolite in a matrix/binder comprising an alumina component. The hydrogenation metal may then be incorporated by impregnation on the catalyst. The hydrogenation metals are selected so as to provide a moderate activity and thereby better control of the exothermicity of the oligomerization step by mainly hydrogenating the dimers being formed as the oligomerization takes place, thereby interrupting the formation of higher oligomers.

Hence, rather than having separate reactors and attendant separation units for conducting oligomerization and subsequent hydrogenation, each with its own catalyst, the present invention enables in a single hydro-oligomerization step the use of less equipment e.g. one single reactor, one type of catalyst, optionally a single separation stage downstream for obtaining the jet fuel. A more efficient and simpler overall process and plant for the conversion of oxygenates such as methanol to jet fuels, particularly SAF, is thereby achieved.

In an embodiment, a stream comprising C8-hydrocarbons resulting from cracked C9-C16 hydrocarbons, is withdrawn from said hydrocarbon stream comprising hydrocarbons boiling in the jet fuel range and added to other processes. For instance, the process according to the invention may cooperate with a refinery plant (or process), in particular a bio-refinery, and the stream comprising C8-hydrocarbons is added to the gasoline pool in a separate process for producing gasoline of said refinery. Optionally, a stream comprising C8-hydrocarbons resulting from cracked C9-C16 hydrocarbons, is withdrawn from said hydrocarbon stream comprising hydrocarbons boiling in the jet fuel range and used (recycled) as additional feed stream to the oligomerization step or the single hydro-oligomerization step.

In a second aspect of the invention, there is also provided a MTO process for producing an olefin stream, said process comprising passing a feedstock stream comprising oxygenates over a catalyst active in the conversion of oxygenates, in which the catalyst comprises a zeolite with a framework having a 10-ring pore structure, in which said 10-ring pore structure is a unidimensional (1-D) pore structure, at a pressure of 1-25 bar, such as 2-25 bar, wherein the feedstock stream is combined with a diluent, the feedstock stream is methanol and it is diluted to a methanol concentration in the feedstock of 2-20 vol. %, preferably 5-10 vol. %, and wherein said 1-D pore structure is any of *MRE (ZSM-48), MTT (ZSM-23), TON (ZSM-22), or combinations thereof.

It would be understood that the range of methanol concentrations and pressure range correspond to operation at partial pressures of methanol ($P_{MeoH}$) in the range: 0.02-5, preferably 0.05-2.5 bar. For example, at pressure (total pressure) of 1 bar and methanol concentration of 2 vol %, the $P_{MeoH}$ is 0.02 bar, while at pressure (total pressure) of bar and methanol concentration of 2 vol %, the $P_{MeoH}$ is 0.5 bar (=25*0.02). At pressure (total pressure) of 1 bar and methanol concentration of 20 vol %, the $P_{MeoH}$ is 0.2 bar, while at pressure (total pressure) of 25 bar and methanol concentration of 20 vol %, the $P_{MeoH}$ is 5 bar (=25*0.2).

By combining the feedstock with the diluent, such as nitrogen or carbon dioxide or a recycle stream of C2-C3 olefins or a C3-olefin comprising e.g. light paraffins, including methane, acting as a diluent, there is a reduction in the exothermicity in the conversion to olefins by the light paraffins acting as a heat-sink, and which is particularly preferred when the catalyst in the MTO is arranged as a fixed bed.

Any of the embodiments of the first aspect of the invention and associated benefits may be used in the second aspect of the invention, or vice versa.

DETAILED DESCRIPTION

Figure 1:
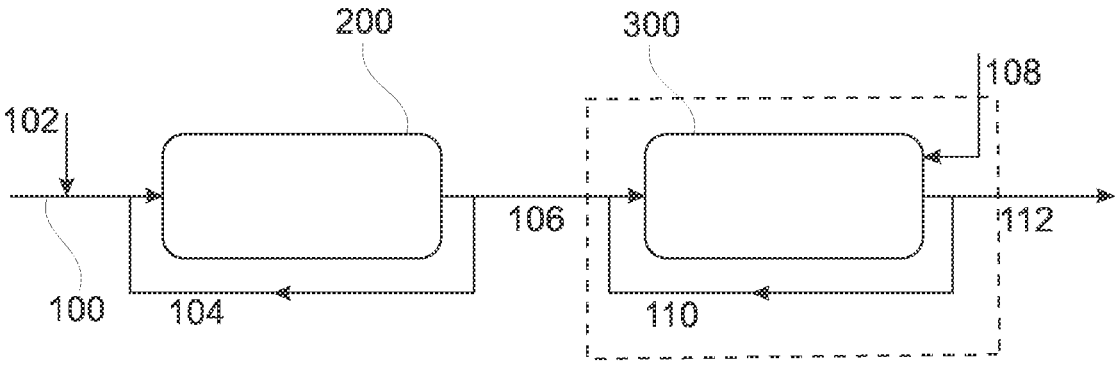
FIG. 1 is a simplified figure showing the conversion of oxygenates to olefins and optional further conversion to jet fuel in accordance with an embodiment of the invention.

With reference to FIG. 1, a feedstock comprising oxygenates 100, such as methanol and/or DME, is directed together with an optional hydrogen stream 102 and an olefin stream 104 comprising C2-C3 olefins which is withdrawn from the olefin stream 106 formed in oxygenate conversion section 200. The oxygenate conversion section 200, for instance a MTO section, converts the oxygenates over a zeolite catalyst such as ZSM-48 having SAR of for instance up to 110 at e.g. 1-15 bar and 260-360° C., e.g. 300-360° C., or 300-350° C. The resulting olefin stream 106 at these conditions is rich in higher olefins (C3=-C8=) and low in aromatics and is optionally further converted (as shown by stippled lines) to a hydrocarbon stream 112 comprising hydrocarbons boiling in the jet fuel range (C8-C16).

This further conversion is conducted in downstream oligomerization and hydrogenation section 300, which preferably is combined as a single hydro-oligomerization step, for instance in a single reactor. The olefin stream 106, suitably after removing its water content, is mixed with optional oligomerization olefin stream 110 comprising C8-hydrocarbons and resulting from cracked C9-C16 hydrocarbons withdrawn from said hydrocarbon stream 112 comprising hydrocarbons boiling in the jet fuel range. The resulting mixed stream is then directed to section 300 and converted, under the presence of hydrogen being fed as stream 108, over a catalyst such as Ni supported on a zeolite having a FAU or MTT structure, for instance Y-zeolite, or ZSM-23, at e.g. 20-40 bar and 50-350° C., to the hydrocarbon stream 112 comprising hydrocarbons boiling in the jet fuel range. At these conditions, particularly the lower pressures, the single reactor in section 300 operates such that the oligomerization is dimerization and optionally also trimerization, and at the same time there is hydrogenation activity. Due to the higher olefins, isoparaffins, low aromatics (e.g. below 1 wt %), low ethylene (e.g. below 1 wt %) of the olefin stream 106, the hydrocarbons in stream 112 boiling in the jet fuel range i.e. jet fuel, can be used as SAF.

Figure 2:
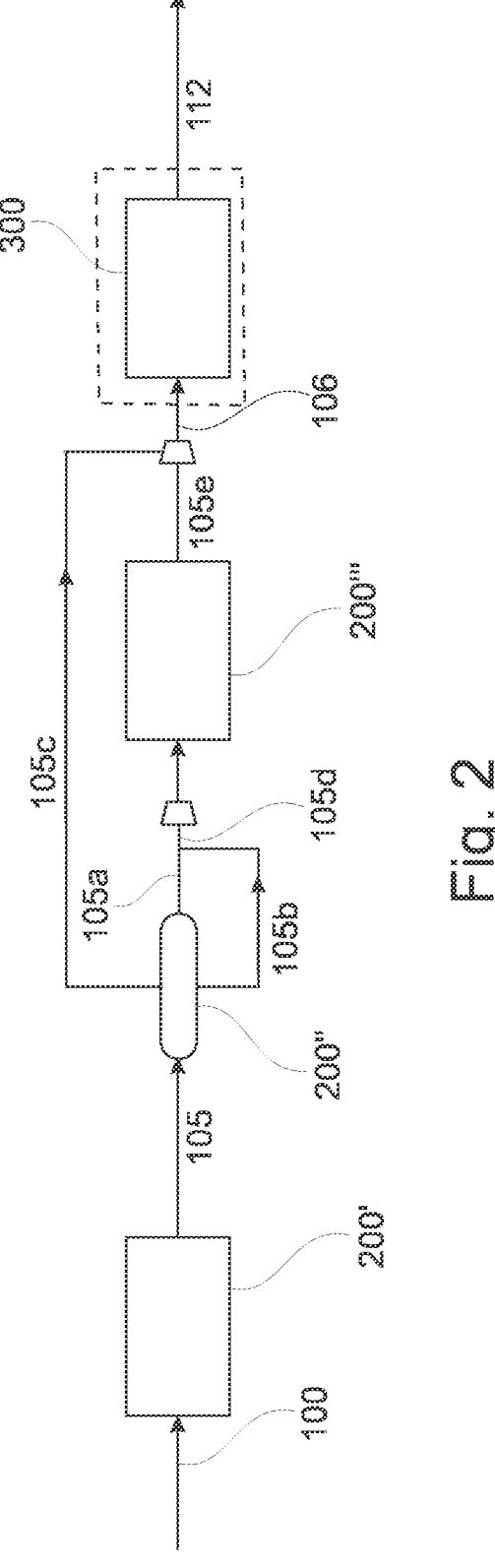
FIG. 2 is a simplified figure showing a particular embodiment of the invention for the conversion a feedstock comprising oxygenates to olefins and optional further conversion to jet fuel.

With reference to FIG. 2, a feedstock stream 100 comprising oxygenates such as methanol and/or DME passes through a first reactor set 200', for instance three reactors arranged in parallel, for thereby achieving 50-70% conversion of the methanol and producing a raw olefin stream 105 comprising water, methanol and olefins e.g. C2-C8 olefins. The raw olefin stream 105 is subjected to separation in 3-phase separator 200'' thereby producing a first olefin stream 105a, which is rich in lower olefins, particularly C2-C3 olefins or mainly C2 olefins (ethylene), a separated oxygenate stream 105b comprising the unconverted oxygenates, e.g. unconverted methanol, and a second olefin stream 105c which is rich in higher olefins, particularly C3-C8 olefins incl. C4-C8 olefins. The first olefin stream 105a is combined with the separated oxygenate stream 105b comprising the unconverted oxygenates, thereby forming a combined stream 105d comprising lower olefins, particularly C2-C3 olefins or mainly ethylene, and the unconverted oxygenates. This combined stream is pressurized and fed to a second reactor set 200''' arranged downstream, and which may for instance include two reactors arranged in parallel, for thereby achieving full conversion e.g. 85% or 90% or higher. The first reactor set 200' and second reactor set 200''' are thereby arranged in series. A third olefin stream 105e is produced which is rich in higher olefins, particularly C3-C8 olefins. Finally, the second olefin stream 105c (bypass stream) is combined with the third olefin stream 105e, thereby forming said olefin stream 106 which may have been pressurized. By the above arrangement of the MTO section 200, the rectors of the first and second set can be operated at low temperature, e.g. 250-350° C. or 260-360° C., suitably at a lower temperature than when using the embodiment of FIG. 1, which helps improving the life-time conversion capacity of the catalysts used and improve the selectivity to higher olefins due to less cracking. The resulting olefin stream 106, suitably after removing its water content, is optionally further converted (as shown by the stippled lines) in a downstream oligomerization and hydrogenation section 300, which is combined as a single hydrooligomerization step, for instance in a single reactor, thereby producing hydrocarbon stream 112 comprising hydrocarbons boiling in the jet fuel range (C8-C16), particularly SAF, as explained in connection with FIG. 1.

EXAMPLES

Example 1. Product Selectivity in MTO

MTO tests were run in a fixed catalyst bed (fixed bed) reactor with a zeolite catalyst ZSM-48 (EU-2) having a 1-D pore structure and a silica to alumina ration (SAR) of 110, and at the following operating conditions: zeolite catalyst load: 250 mg cat/750 mg SiC, pressure=1 barg (2 bar), space velocity (WHSV)=2 h$^{-1}$, total flow=3.5 NL/h (59 mL/min); methanol concentration in the feed ($C_{MeOH}$)=10% (volume basis) with nitrogen as the diluent. Thus, $P_{MeOH}$ is 0.2 bar. The temperature used is in the range 320-360° C.

Figure 3:
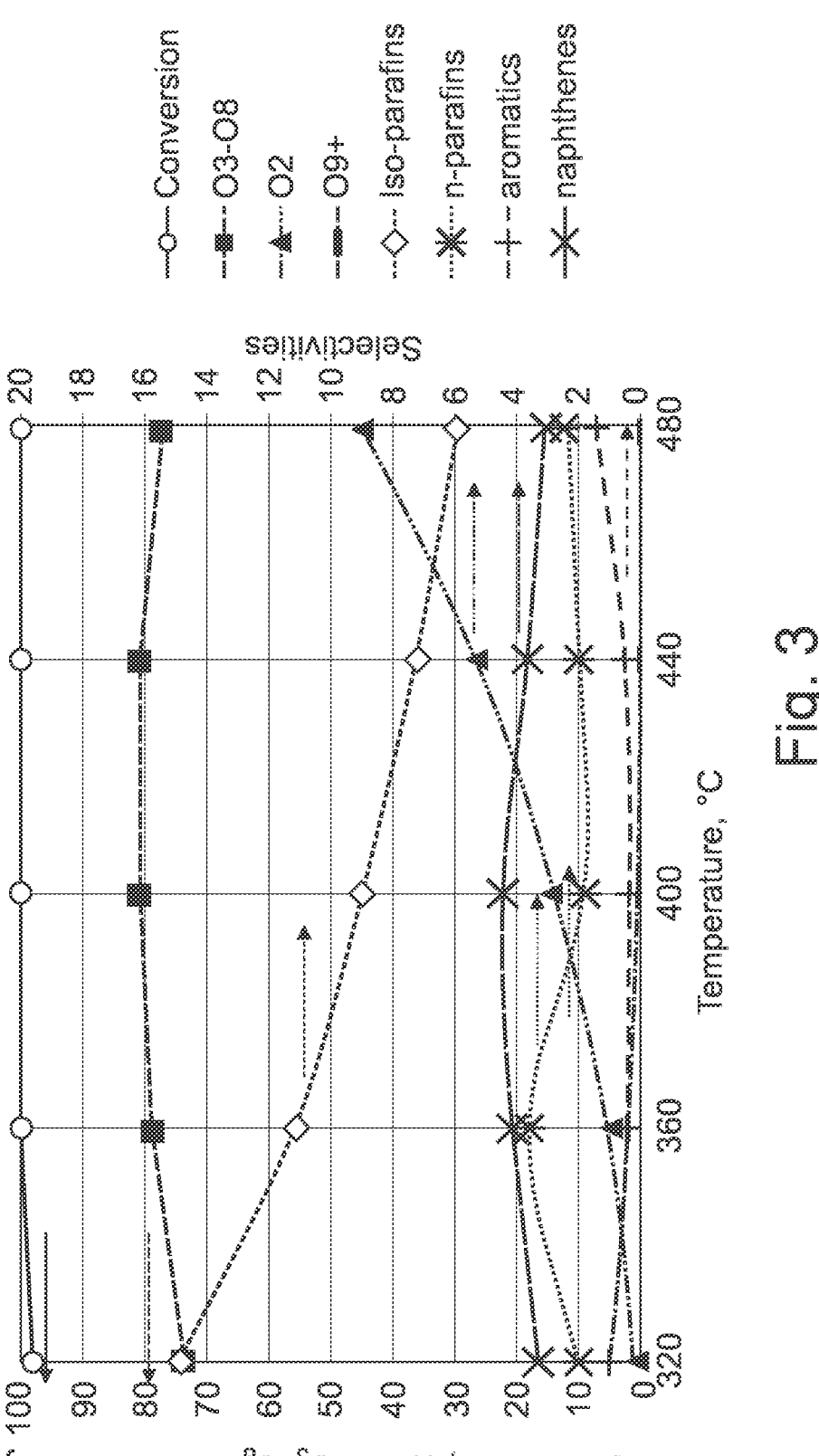
FIG. 3 shows a plot of methanol conversion and C3-C8 selectivity as a function of the temperature in accordance with Example 1

FIG. 3 shows the methanol conversion as a function of temperature. It is observed, that already at 320° C., there is almost 100% conversion, and at 360° C. there is 100% conversion. Aromatics are formed but are kept at a low level, namely below 1 wt %, more specifically at about 0.5 wt % at 360° C. and near 1 wt % at 320° C. Hence, there is low selectivity towards formation of aromatics. At the same time, the content of isoparaffins in the olefin stream increases with decreasing temperatures to a range of 10-15 wt % in the temperature window 320-360° C., while the content of the C2-olefin (ethylene, in the figure denoted as O2) decreases with temperature and becomes 1 wt % or less in the same temperature window, thus providing an olefin stream free of ethylene. For instance, at 320° C., the ethylene content is as low as 0.2 wt %. The content of higher olefins (C3-C8, in the figure denoted as O3-O8) is kept at a high level, namely in the range 70-80 wt % of the olefin stream. Olefins having more than nine (9) carbons (in the figure denoted as O9+) are also maintained at a low level.

The table below shows the olefin distribution in wt % in the olefin stream.

| T (° C.) | C2= | C3= | C4= | C5= | C6= | C7= | C8= and C9= |
|---|---|---|---|---|---|---|---|
| 320 | <1 | 21 | 27 | 28 | 15 | 7 | 1 |
| 360 | 1 | 31 | 28 | 26 | 9 | 4 | 1 |
| 400 | 2 | 37 | 28 | 25 | 5 | 3 | n.d.* |

-continued

| T (° C.) | C2= | C3= | C4= | C5= | C6= | C7= | C8= and C9= |
|---|---|---|---|---|---|---|---|
| 440 | 6 | 47 | 24 | 18 | 3 | 2 | n.d.* |
| 480 | 11 | 50 | 22 | 13 | 2 | 2 | n.d.* |

*not detectable

Figure 4:
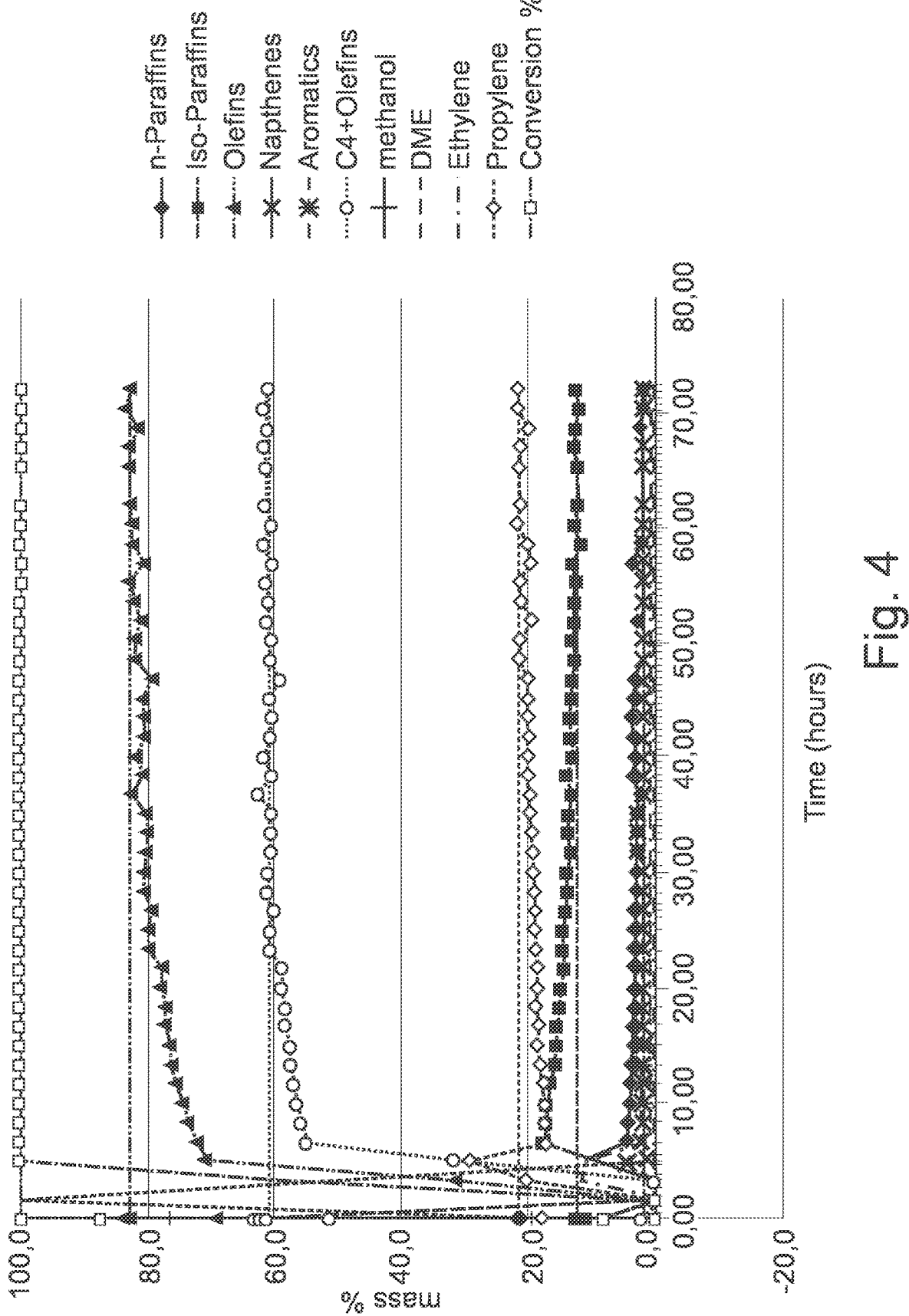
FIG. 4 shows a plot of the methanol conversion and yields as a function of cycle time of the catalyst (hours-on-stream, HOS) at the specific temperature of 360° C., in accordance with Example 1.

FIG. 4 shows the methanol conversion and yields (mass,% in Y-axis) in terms of time on stream (time in hours in X-axis) at the specific temperature of 360° C. It is observed that the catalyst cycle time is maintained over prolonged periods, thus making it suitably for commercial application i.e. industrial application.

Compared to the prior art according to U.S. Pat. No. 4,476,338, where MTO is conducted over a ZSM-48 having SAR of 113 or 180 and at 370° C. (Example 1 and 2 therein), the olefin stream according to the present invention enables a higher production of total olefins (e.g. C2-C8 olefins); lower production of ethylene, for instance the content of ethylene now being less than 1 wt %; lower production of aromatics, for instance the content of aromatic compounds now being below 1 wt %; and higher production of isoparaffins, for instance now 10-15 wt %. Furthermore, the catalyst lifetime is increased.

Example 2. Effect of Binder in the Catalyst in MTO

The same tests with ZSM-48 (EU-2) where conducted at WSHV=2 h$^{-1}$, methanol concentration in the feed ($C_{MeOH}$)=8% (volume basis) with nitrogen as diluent and pressure of 5 bar, using a catalyst with a binder: 60 wt % zeolite and 40 wt % alumina. The table below shows the effect of adding the binder.

At high temperatures i.e. above 360° C. such as 400, 440 or 480° C., as shown in the table, a high amount of paraffins is formed, almost exclusively as methane, which is highly likely a result of MeOH/DME cracking i.e. MeOH and/or DME cracking. At lower temperatures corresponding to the present invention (360° C.), the cracking becomes negligible, resulting in an effective conversion of the DME/MeOH into olefins.

| Temperature, C. | MeOH conversion, % | Olefin yield, wt % | Paraffin yield, wt % | Methane yield, wt. % |
|---|---|---|---|---|
| 480 | 100 | 45 | 48 | 48 |
| 440 | 100 | 68 | 23 | 23 |
| 400 | 100 | 80 | 6 | 6 |
| 360 | 96 | 80 | 2 | 1 |

Example 3. Effect of Methanol Partial Pressure in MTO

Figure 5:
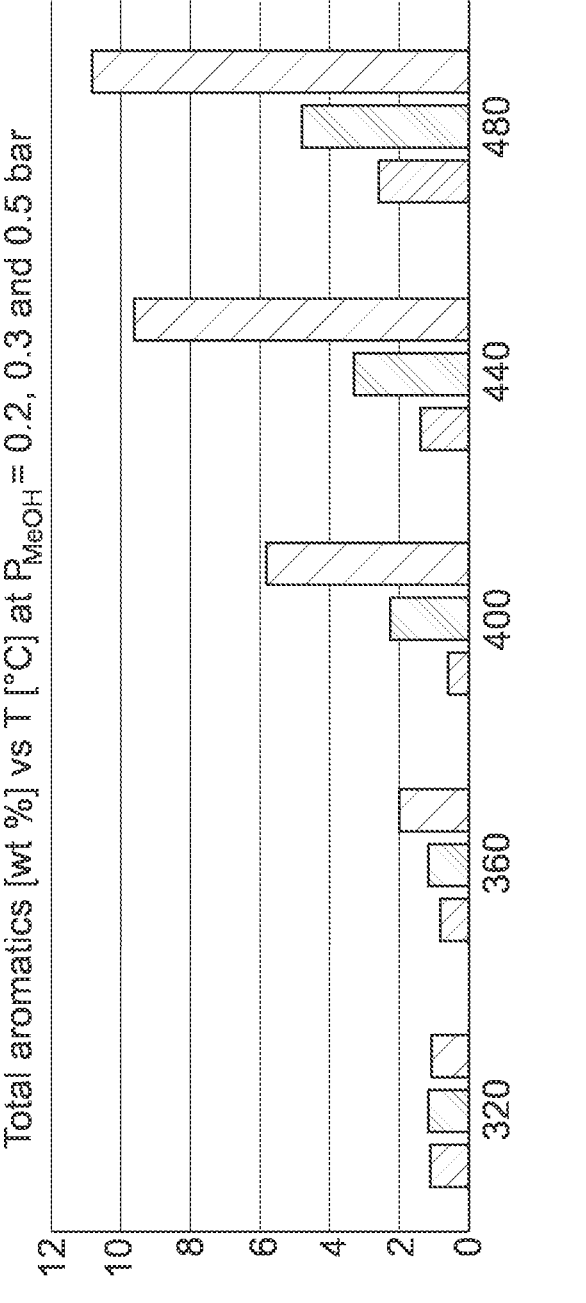
FIG. 5 shows a plot of the content of aromatics in the olefin stream at different temperatures as well as a function of methanol partial pressures ($P_{MeoH}$), in accordance with Example 3

The same tests with ZSM-48 (EU-2) where conducted at WSHV=2 h$^{-1}$ and methanol concentration in the feed ($C_{MeOH}$)=10% (volume basis). FIG. 5 shows the content of aromatics (total aromatics, wt %) measured as benzene (B), toluene (T), xylene (X) and ethylbenzene (Total aromatics), at the different temperatures as well as a function of methanol partial pressures $P_{MeOH}$ at the different temperatures. At a given temperature, for instance at 320° C., each column designates a $P_{MeOH}$: the column in the left is $P_{MeOH}$=0.2 bar, the column in the center $P_{MeOH}$=0.3 bar and the column in the right $P_{MeOH}$=0.5 bar. At a methanol concentration in the feed of 10%, the pressure (total pressure) at each give partial pressure is respectively: 2 bar, 3 bar and 5 bar.

It is observed that is that at low temperature, from 360° C. and below, the MeOH partial pressure does not seem to have any significant influence on the content of aromatics in the resulting olefin stream. The (negative) effect of high MeOH partial pressure in terms of higher production of aromatics, thus appears to decrease drastically at 360° C. and more or less vanish at temperatures below about 350° C. This enables an increase in the pressure used for conducting MTO, which provides benefits in terms of i.a. higher throughout in the MTO and reduction of equipment size in the plant for producing SAF.

As shown in FIG. 5, at the lower temperatures, the content of aromatics is maintained below 2 wt % and at similar values regardless of the $P_{MeOH}$. For instance, with MTO operating at 400° C., at $P_{MeOH}$ of 0.3 and 0.5 the content of aromatics is about 2 wt % and 6 wt %, respectively. When operating the MTO at 360° C., at $P_{MeOH}$ of 0.3 and 0.5 the content of aromatics is about 1 wt % and 2 wt %, respectively. When operating the MTO at 320° C., at $P_{MeOH}$ of 0.3 and 0.5 the content of aromatics is about 1 wt % at both $P_{MeOH}$.

When co-feed of light olefins such as the C3-olefin (propylene) is provided, see Example 4, this enables a further reduction in temperature and, in turn, a further reduction in hydrogen transfer (less generation of e.g. aromatics), higher olefin chain length and, additionally, more freedom with respect to total (or methanol partial) pressure extend ultimate catalyst longevity.

Example 4. Effect of Lower Olefin Co-Feed in MTO

Figure 6:
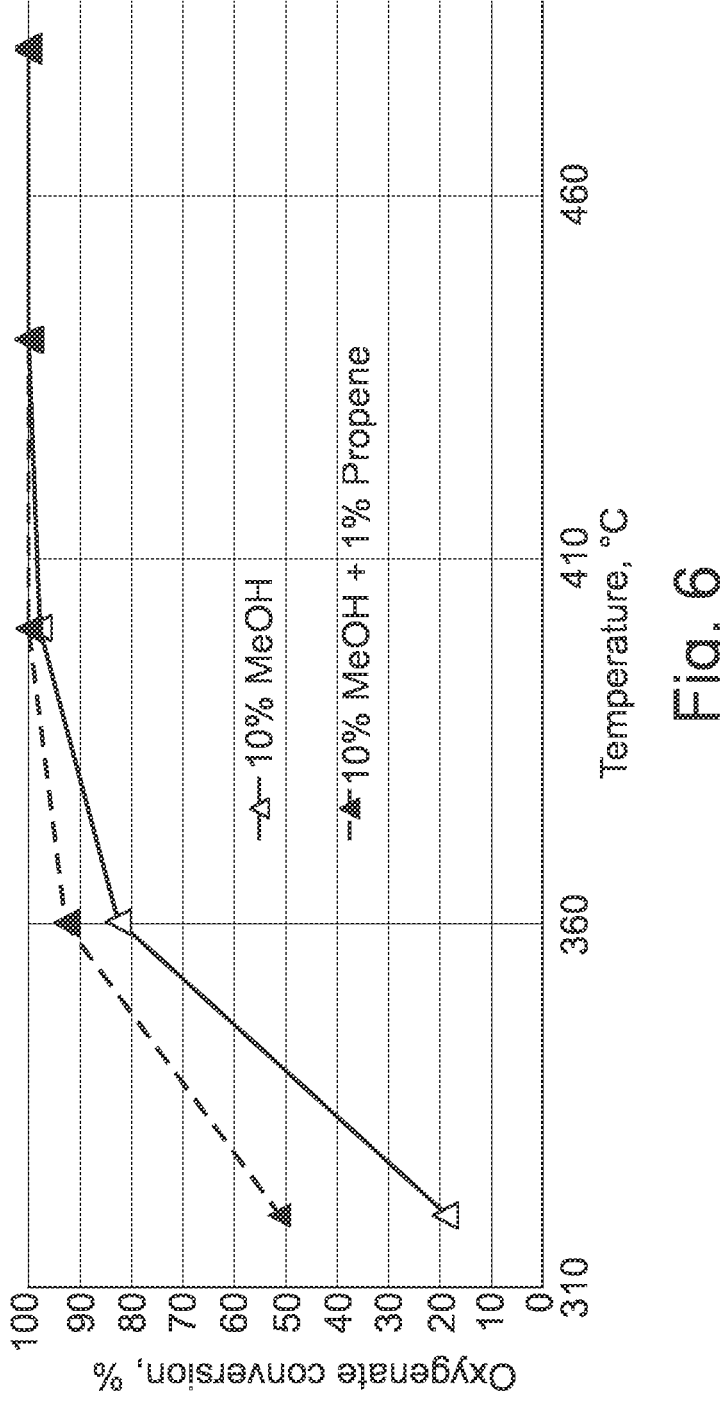
FIG. 6 shows a plot of methanol conversion as a function of temperature with a neat feed of methanol compared to a feed comprising propylene as co-feed, in accordance with Example 4

The effect of adding the lower olefin propylene (propene) into the methanol feed, is shown in FIG. 6.

The comparison is conducted with the same zeolite ZSM-48 (EU-2) at the same reaction conditions in the MTO with 1 mole % propylene (propene), and without (i.e. neat methanol feed). Operating conditions: zeolite catalyst load: 250 mg cat/750 mg SiC, pressure=2 barg (3 bar), space velocity (WHSV)=2 h$^{-1}$, total flow=3.5 NL/h (59 mL/min); methanol concentration in the feed ($C_{MeOH}$)=10% (volume basis) with nitrogen as the diluent.

FIG. 6 shows that adding propylene as co-feed (upper line in the figure) significantly promotes the kick-off or initiation of the oxygenate (methanol) conversion. In the operation of the MTO, there will be significant amounts of light olefins, namely C2-C3 olefins, in the recycle stream, suitably as a portion of the olefin stream, and which may be utilized anyway for temperature control in the MTO due to its exothermicity. The addition of the lower olefin, e.g. as recycle stream, to the methanol feed enables a significant reduction of the inlet temperature to the MTO, whereby the content of aromatics and paraffins (as used herein, also incl. methane) decreases, while the average olefin chain length increases—and hence the content of higher olefins. Furthermore, the co-feed with the lower olefin significantly increases catalyst longevity, for instance as measured by catalyst cycle time. Moreover, hydrogen transfer reactions are minimized, and not least the lower temperature of the MTO, e.g. 320° C., enables operation at the higher pressure range, which may be also advantageous, as described in connection with Example 3.

The invention claimed is:

1. A process for producing an olefin stream, said process comprising:
   passing a feedstock stream comprising oxygenates over a catalyst active in the conversion of oxygenates, in which the catalyst comprises a zeolite with a framework having a 10-ring pore structure that is a unidimensional (1-D) pore structure, at a pressure of 1-25 bar and a temperature of 240-360° C. to produce an effluent stream comprising olefins and water; and
   removing water from the effluent stream to obtain the olefin stream,
   wherein said 1-D pore structure is any of *MRE (ZSM-48), MTT (ZSM-23), TON (ZSM-22), or combinations thereof,
   wherein the feedstock stream comprises a diluent and methanol, wherein a methanol concentration in the feedstock stream is 2-20 vol. %,
   wherein the olefin stream is essentially free of aromatics by comprising less than 5 wt % aromatics, wherein the olefin stream comprises 50 wt % or greater of C3-C8 olefins and 1 wt % or less of ethylene, and
   wherein the process further comprises recycling a portion of an olefin-containing stream to the feedstock stream.

2. The process according to claim 1, wherein the catalyst comprises a binder selected from the group of refractory oxides and clays.

3. The process according to claim 2, wherein the catalyst comprises 30-90 wt % zeolite, and wherein the binder comprises an alumina component.

4. The process according to claim 3, wherein the catalyst contains 50-80 wt % zeolite with the binder.

5. The process according to claim 1, wherein the zeolite has a silica-to-alumina ratio (SAR) of up to 240.

6. The process according to claim 1, wherein said portion of the olefin-containing stream is a stream comprising C2-C3 olefins or a C3 olefin stream which is withdrawn from said olefin stream.

7. The process according to claim 1, wherein the feedstock stream comprising oxygenates is derived from one or more oxygenates taken from the group consisting of triglycerides, fatty acids, resin acids, ketones, aldehydes or alcohols or ethers, where said oxygenates originate from one or more of a biological source, a gasification process, a pyrolysis process, Fischer-Tropsch synthesis, or methanol-based synthesis.

8. The process according to claim 1, comprising: using a first reactor set including a single reactor or several reactors, for a partial or full conversion of the oxygenates.

9. The process according to claim 8, further comprising using a second reactor set including a single reactor or several reactors, for further conversion of unconverted oxygenates, and a phase separation stage in between the first reactor set and the second reactor set.

10. The process according to claim 9, comprising:
   passing the feedstock stream comprising oxygenates through the first reactor set under conditions for partly converting the oxygenates, thereby forming a raw olefin stream comprising unconverted oxygenates and C2-C8 olefins;
   passing the raw olefin stream through said phase separation stage, for producing:
   a first olefin stream comprising 50 wt % or greater of C2 olefins;
   a separated oxygenate stream comprising unconverted oxygenates;

a second olefin stream comprising 50 wt % or greater of C3-C8 olefins;

combining the first olefin stream with the separated oxygenate stream comprising the unconverted oxygenates, thereby forming a combined stream comprising lower olefins and the unconverted oxygenates;

passing the resulting combined stream comprising lower olefins and the unconverted oxygenates through the second reactor set under conditions for fully converting the unconverted oxygenates and the lower olefins, into a third olefin stream comprising 50 wt % or greater of C3-C8 olefins; and combining the second olefin stream with the third olefin stream, thereby forming said effluent stream.

11. The process according to claim 1, further comprising:
passing at least a portion of the olefin stream, through an oligomerization step over an oligomerization catalyst, and optionally subsequently conducting a separation step, for thereby producing an oligomerized stream.

12. The process according to claim 11, further comprising:
passing at least a portion of the oligomerized stream through a hydrogenation step over a hydrogenation catalyst, and optionally subsequently conducting a separation step, for thereby producing a hydrocarbon stream comprising hydrocarbons boiling in the jet fuel range.

13. The process according to claim 11, wherein the oligomerization step and hydrogenation step are combined in a single hydro-oligomerization step, wherein the oligomerization step is dimerization, optionally also trimerization, by the hydro-oligomerization step being conducted by reacting, under the presence of hydrogen, the olefin stream, over a catalyst comprising a hydrogenation metal.

14. The process according to claim 1, wherein the olefin stream is passed directly to the oligomerization step.

15. The process according to claim 1, wherein the olefin stream comprises at least 70 wt % C3-C8 olefins.

16. The process according to claim 15, wherein the olefin stream further comprises:
1 wt % or less of aromatics.

17. The process according to claim 15, wherein the temperature is 320-360° C.

18. The process according to claim 1, wherein the distribution of olefins in the olefin stream is at least 67 wt % C4-C7 olefins.

19. A process for producing an olefin stream, said process comprising:
passing a feedstock stream comprising oxygenates over a catalyst active in the conversion of oxygenates, in which the catalyst comprises a zeolite with a framework having a 10-ring pore structure that is a unidimensional (1-D) pore structure, at a pressure of 1-25 bar and a temperature of 240-360° C. to produce an effluent stream comprising olefins and water; and
removing water from the effluent stream to obtain the olefin stream; and
wherein said 1-D pore structure is any of *MRE (ZSM-48), MTT (ZSM-23), TON (ZSM-22), or combinations thereof, and
wherein the feedstock stream comprises a diluent and methanol, wherein a methanol concentration in the feedstock stream is 2-20 vol. %, and
wherein the process further comprises separating from the olefin stream an isoparaffin stream.

20. The process according to claim 19, further comprising:
passing at least a portion of the olefin stream, after separating said isoparaffin stream, through an oligomerization step over an oligomerization catalyst, and optionally subsequently conducting a separation step, for thereby producing an oligomerized stream.

21. The process according to claim 19, wherein the entire olefin stream after separating said isoparaffin stream is passed directly to the oligomerization step.

22. A process for producing an olefin stream, said process comprising:
passing a feedstock stream comprising oxygenates over a catalyst active in the conversion of oxygenates, in which the catalyst comprises a zeolite with a framework having a 10-ring pore structure that is a unidimensional (1-D) pore structure, at a pressure of 1-25 bar, and a temperature of 240-360° C. to produce an effluent stream comprising olefins and water; and
removing water from the effluent stream to obtain the olefin stream,
wherein said 1-D pore structure is any of *MRE (ZSM-48), MTT (ZSM-23), TON (ZSM-22), or combinations thereof,
wherein the olefin stream is essentially free of aromatics by comprising less than 5 wt % aromatics, wherein the olefin stream comprises 50 wt % or greater of C3-C8 olefins and 1 wt % or less of ethylene, and
wherein the process further comprises recycling a portion of an olefin-containing stream to the feedstock stream.

23. The process according to claim 22, wherein the oxygenates are selected from methanol (MeOH), dimethyl ether (DME), or combinations thereof.

24. The process according to claim 22, wherein the feedstock stream comprises a diluent and methanol, wherein a methanol concentration in the feedstock stream is 5-10 vol. %.

* * * * *